(12) United States Patent
Chaulagain et al.

(10) Patent No.: US 9,777,118 B2
(45) Date of Patent: Oct. 3, 2017

(54) METHODS OF MANUFACTURE OF SALTS OF HYDROXY-SUBSTITUTED AROMATIC COMPOUNDS AND POLYETHERIMIDES

(71) Applicant: SABIC GLOBAL TECHNOLOGIES B.V., Bergen op Zoom (NL)

(72) Inventors: Mani Raj Chaulagain, Evansville, IN (US); Farid Fouad Khouri, Clifton Park, NY (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/304,134

(22) PCT Filed: Apr. 15, 2015

(86) PCT No.: PCT/US2015/025943
§ 371 (c)(1),
(2) Date: Oct. 14, 2016

(87) PCT Pub. No.: WO2015/160929
PCT Pub. Date: Oct. 22, 2015

(65) Prior Publication Data
US 2017/0029569 A1 Feb. 2, 2017

Related U.S. Application Data

(60) Provisional application No. 61/979,810, filed on Apr. 15, 2014.

(51) Int. Cl.
*C08G 73/10* (2006.01)
*C07C 37/66* (2006.01)
*C08K 5/31* (2006.01)

(52) U.S. Cl.
CPC .......... *C08G 73/1071* (2013.01); *C07C 37/66* (2013.01); *C08G 73/10* (2013.01); *C08G 73/1003* (2013.01); *C08K 5/31* (2013.01)

(58) Field of Classification Search
CPC .... C08G 73/107; C08G 73/1003; C08G 8/02; C07C 37/66; C07G 1/02; C07D 401/00
See application file for complete search history.

(56) References Cited

U.S. PATENT DOCUMENTS

| 4,202,993 A | 5/1980 | Takekoshi |
| 4,410,735 A | 10/1983 | Dellacoletta et al. |

(Continued)

FOREIGN PATENT DOCUMENTS

| CN | 1073071 C | 10/2001 |
| CN | 1367192 A | 9/2002 |

(Continued)

OTHER PUBLICATIONS

International Search Report for International Application No. PCT/US2015/025943, International Application Filing Date: Apr. 15, 2015, Date of Mailing: Jul. 2, 2015; 4 pages.

(Continued)

*Primary Examiner* — Shane Fang
(74) *Attorney, Agent, or Firm* — Cantor Colburn LLP

(57) ABSTRACT

A method for the manufacture of a metal salt of a hydroxy-substituted aromatic compound comprises: contacting a hydroxy-substituted aromatic compound with a base comprising a metal cation in molten diphenyl sulfone or sulfolane to provide a mixture comprising water, diphenyl sulfone or sulfolane, and a metal salt of the hydroxy-substituted aromatic compound; and removing water from the mixture in the absence of an azeotrope solvent to provide the metal salt of the hydroxy-substituted aromatic compound that contains less than 3,000 ppm of water.

15 Claims, 2 Drawing Sheets

(56) References Cited

U.S. PATENT DOCUMENTS

| | | | |
|---|---|---|---|
| 4,492,806 A | 1/1985 | Mendiratta et al. | |
| 4,546,207 A | 10/1985 | Mendiratta et al. | |
| 4,870,155 A | 9/1989 | Matzner et al. | |
| 5,229,482 A | 7/1993 | Brunelle | |
| 5,266,679 A | 11/1993 | Perry et al. | |
| 5,514,813 A | 5/1996 | Brunelle | |
| 5,663,275 A | 9/1997 | Schmidhauser | |
| 5,830,974 A | 11/1998 | Schmidhauser et al. | |
| 5,856,421 A | 1/1999 | Schmidhauser | |
| 5,908,915 A | 6/1999 | Brunelle | |
| 6,066,743 A | 5/2000 | Nick et al. | |
| 6,096,900 A | 8/2000 | Nick et al. | |
| 6,235,866 B1 | 5/2001 | Khouri et al. | |
| 6,265,521 B1 | 7/2001 | Fyvie et al. | |
| 6,849,706 B1 | 2/2005 | Brunelle et al. | |
| 6,906,168 B2 | 6/2005 | Khouri et al. | |
| 6,919,418 B2 | 7/2005 | Khouri et al. | |
| 7,115,785 B2 | 10/2006 | Guggenheim et al. | |
| 7,125,954 B2 | 10/2006 | Guggenheim et al. | |
| 7,481,959 B2 | 1/2009 | Richards et al. | |
| 7,605,222 B2 | 10/2009 | Ye et al. | |
| 7,705,190 B2 | 4/2010 | Brunelle | |
| 7,714,095 B2 | 5/2010 | Brunelle et al. | |
| 7,902,407 B2 | 3/2011 | Silva et al. | |
| 7,981,996 B2 | 7/2011 | Khouri et al. | |
| 2005/0049439 A1* | 3/2005 | Guggenheim | C07C 37/66 568/718 |
| 2005/0272957 A1 | 12/2005 | Gao et al. | |
| 2006/0135741 A1 | 6/2006 | Gui et al. | |
| 2009/0163691 A1 | 6/2009 | Bernabe et al. | |
| 2011/0263791 A1 | 10/2011 | Chiong et al. | |
| 2013/0108851 A1 | 5/2013 | Kuhlman et al. | |
| 2014/0099510 A1 | 4/2014 | Chiong et al. | |

FOREIGN PATENT DOCUMENTS

| | | |
|---|---|---|
| CN | 1396194 A | 2/2003 |
| CN | 1560113 A | 1/2005 |
| CN | 1563150 A | 1/2005 |
| CN | 1803888 A | 7/2006 |
| CN | 101235009 A | 8/2008 |
| CN | 101628977 A | 1/2010 |
| CN | 101704950 A | 5/2010 |
| CN | 101735022 A | 6/2010 |
| CN | 103159593 A | 6/2013 |
| DE | 2335687 A1 | 2/1975 |
| DE | 4129546 C1 | 4/1993 |
| EP | 0117459 B1 | 9/1989 |
| EP | 0857710 A1 | 8/1998 |
| EP | 2233512 B1 | 3/2013 |
| GB | 2280183 A | 1/1995 |
| JP | S63159332 A | 7/1988 |
| RO | 107949 B1 | 1/1994 |

OTHER PUBLICATIONS

Written Opinion for International Application No. PCT/US2015/025943, International Application Filing Date: Apr. 15, 2015; Date of Mailing: Jul. 2, 2015, 5 pages.

Shang et al, "One-Pot Synthesis of Polyetherimides from Bis(chlorophthalimide) and Dichlorodiphenylsulfone in Diphenylsulfone", Journal of Applied Polymer Science, vol. 102, 2006, pp. 4584-4588.

* cited by examiner

METHODS OF MANUFACTURE OF SALTS OF HYDROXY-SUBSTITUTED AROMATIC COMPOUNDS AND POLYETHERIMIDES

CROSS REFERENCE TO RELATED APPLICATIONS

This application is a National Stage application of PCT/US15/25943, filed Apr. 15, 2015, which claims the benefit of U.S. Provisional Application No. 61/979,810, filed Apr. 15, 2014, both of which are incorporated by reference in their entirety herein.

BACKGROUND

This disclosure is directed to a method for the manufacture of salts of hydroxy-substituted aromatic compounds, particularly to the manufacture of alkali metal salts of hydroxy-substituted aromatic compounds. The disclosure is also directed to the manufacture of polyetherimides from the prepared salts of hydroxy-substituted aromatic compounds.

Salts of hydroxy-substituted aromatic compounds find varied uses in the industry. For example, bisphenol dialkali salts can be used for the synthesis of polyetherimides via displacement polymerizations.

The existing methods to prepare bisphenol dialkali salts typically use a significant amount of azeotropic solvents such as xylenes, ortho-dichlorobenzene, or toluene in order to remove water, either produced as a byproduct of the reaction, or present in the reaction mixture as a solvent or co-solvent, through azeotropic distillation. To reduce cost, it would be desirable to avoid using azeotropic solvents in the process. Accordingly, there exists a need for a simplified method to prepare salts of hydroxy-substituted aromatic compounds without using azeotropic solvents.

SUMMARY

Disclosed is a method for the manufacture of a metal salt of a hydroxy-substituted aromatic compound. The method comprises: contacting a hydroxy-substituted aromatic compound with a base comprising a metal cation in molten diphenyl sulfone or sulfolane to provide a mixture comprising water, diphenyl sulfone, or sulfolane, and a metal salt of the hydroxy-substituted aromatic compound; and removing water from the mixture in the absence of an azeotrope solvent to form the metal salt of the hydroxy-substituted aromatic compound, wherein the metal salt of the hydroxy-substituted aromatic compound comprises less than 3,000 ppm of water.

Also disclosed is a method for the manufacture of a polyetherimide composition comprising: polymerizing a substituted bis(phthalimide) and the metal salt of the dihydroxy aromatic compound of any one or more of Embodiments 1 to 15 in the presence of diphenyl sulfone, sulfolane, or a combination comprising at least one of the foregoing solvent to form a polyetherimide composition.

The above-described and other features are exemplified by the following Drawings, Detailed Description, and Examples.

BRIEF DESCRIPTION OF THE DRAWINGS

A description of the figures, which are meant to be exemplary and not limiting, is provided in which.

Figure 1:
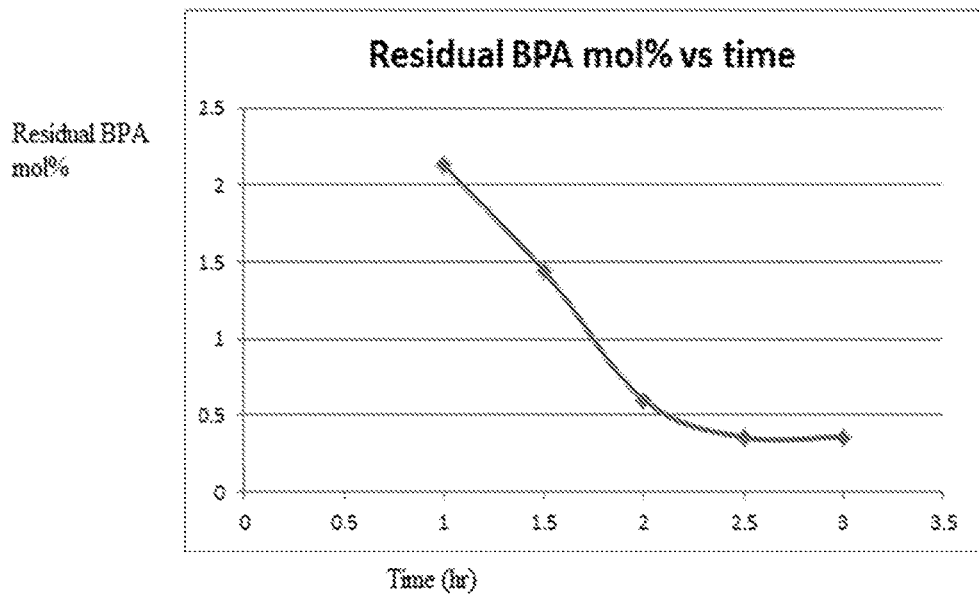
FIG. 1 is a graph of molar percent of residual BPA as a function of time.

The above described and other features are exemplified by the following detailed description and Examples.

DETAILED DESCRIPTION

The inventors hereof have found that salts of hydroxy-substituted aromatic compounds can be prepared in molten diphenyl sulfone, sulfolane, or a combination comprising at least one of the foregoing from hydroxy-substituted aromatic compounds and bases without using azeotropic solvents. In particular, the methods allow the synthesis of potassium or sodium bisphenol A salts in molten diphenyl sulfone, sulfolane, or a combination comprising at least one of the foregoing from bisphenol A and sodium or potassium hydroxide pellets without the use of solvents such as xylenes, ortho-dichlorobenzene, or toluene. Water generated from the salt forming reaction can be completely and conveniently removed by distillation. The stoichiometry of the reaction can be readily monitored and adjusted if necessary. The salts formed from the methods can be used directly in subsequent reactions such as displacement polymerization.

The hydroxy-substituted aromatic compound can be a monohydroxy-substituted aromatic compound; a dihydroxy-substituted aromatic compound; a trihydroxy-substituted aromatic compound; a tetrahydroxy-substituted aromatic compound, or a combination comprising at least one of the foregoing. Monohydroxy-substituted aromatic compounds are illustrated by phenol, p-cresol, p-cumylphenol, and the like. Dihydroxy-substituted aromatic compounds are illustrated by dihydroxybenzenes such as hydroquinone, resorcinol, and the like. Dihydroxy-substituted aromatic compounds are further illustrated by bisphenols such as bisphenol A and biphenols such as 4,4'-dihydroxybiphenyl. Trihydroxy-substituted aromatic compounds are illustrated by 1,3-5-trihydroxybenzene; 1,1,1-tris(4-hydroxyphenyl)ethane (THPE); and the like. Tetrahydroxy-substituted aromatic compounds are illustrated by 2,2-bis(3,4-dihydroxyphenyl)propane; 3,4,3',4'-tetrahydroxybiphenyl; and the like.

In some embodiments, the dihydroxy-substituted compound is an aromatic $C_{6-24}$ monocyclic or polycyclic dihydroxy aromatic compound optionally substituted with 1 to 6 $C_{1-8}$ alkyl groups, 1 to 8 halogen atoms, or a combination thereof, for example a dihydroxy aromatic compound of formula (1):

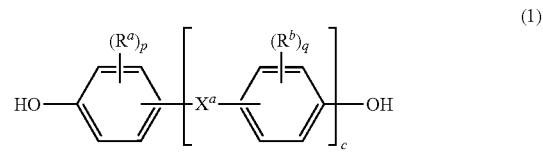

wherein $R^a$ and $R^b$ are each independently a halogen atom or a monovalent hydrocarbon group and can be the same or different; p and q are each independently integers of 0 to 4; c is zero to 4, specifically 0 or 1; and $X^a$ is a bridging group connecting the two aromatic groups, where the bridging group and point of attachment of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a C$_{1-18}$ organic bridging group. The C$_{1-18}$ organic bridging group can be cyclic or acyclic, aromatic or non-aromatic, and can further comprise heteroatoms such as halogens, oxygen, nitrogen, sulfur, silicon, or phosphorous. The C$_{1-18}$ organic group can be disposed such that the C$_6$ arylene groups connected thereto are each connected to a common alkylidene carbon or to different carbons of the C$_{1-18}$ organic bridging group. A specific example of a dihydroxy-substituted compound is of formula (1a)

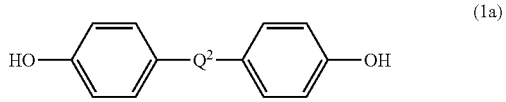

(1a)

wherein Q$^2$ is a single bond, —O—, —S—, —C(O)—, —SO$_2$—, —SO—, —C$_y$H$_{2y}$—, and a halogenated derivative thereof wherein y is an integer from 1 to 5, including perfluoroalkylene groups. In a specific embodiment Q$^2$ is 2,2-isopropylidene and the dihydroxy-substituted aromatic compound is bisphenol A. In another specific embodiment Q$^2$ is a single bond and the dihydroxy-substituted aromatic compound is 4,4'-dihydroxybiphenyl.

The base comprising a metal cation includes a metal hydroxide such as alkali metal hydroxide and alkaline-earth metal hydroxide (alkali hydroxide), alkali metal carbonate and alkali-earth metal carbonate (alkali carbonate), alkali metal bicarbonate and alkali earth-metal bicarbonate (alkali bicarbonate), or a combination comprising at least one of the foregoing. In some embodiments an alkali metal hydroxide is employed as the base comprising a metal cation. In yet another embodiment the base used is sodium hydroxide or potassium hydroxide.

A solid base can be used. Illustrative, non-limiting examples of solid bases comprise solid alkali hydroxides, solid alkali bicarbonates, solid alkali bicarbonates, or a combination comprising at least one of the foregoing. Solid sodium hydroxide and potassium hydroxide are specifically mentioned.

In various embodiments the contacting of the hydroxy-substituted aromatic compound with the base can be performed using stoichiometric amounts wherein the base and the hydroxy-substituted aromatic compound are present in amounts corresponding to a molar ratio of base to hydroxy-substituted aromatic compound which in some embodiments deviates from ideal stoichiometry by no more than 5.0 mol %, by no more than 3.0 mol %, by no more than 2.0 mole %, by no more than 1.0 mole %, by no more than 0.4 mole %, or by no more than 0.2 mole %. In a preferred embodiment the molar ratio deviates from ideal stoichiometry by no more than 0.2 mole %. The deviation can be in either direction, i.e., excess base or excess hydroxy-substituted aromatic compound.

In some embodiments, the amount of diphenyl sulfone, or sulfolane, or a combination comprising at least one of the foregoing is adjusted based on the amount of the hydroxy-substituted aromatic compound. In particular, the amount is based on the weight of the hydroxy-substituted aromatic compound divided by the sum of the weight of the hydroxy-substituted aromatic compound plus the weight of the diphenyl sulfone, sulfolane, or a combination comprising at least one of the foregoing as follows:

$$\frac{\text{weight of hydroxy-substituted aromatic compound}}{\text{weight of hydroxy-substituted aromatic compound} + \text{weight of diphenyl sulphone or sulfolane}}(100)$$

and can be 1 to 30%, specifically 15 to 25%, or 18 to 22%.

In some embodiments, diphenyl sulfone, sulfolane, or a combination comprising at least one of the foregoing is present in an amount of 10 wt. % to 95 wt. % based on the sum of the weights of the hydroxy-substituted compound and the base.

The contacting of the hydroxy-substituted aromatic compound is performed in molten diphenyl sulfone, sulfolane, or a combination comprising at least one of the foregoing at a temperature that is greater than the melting point of the diphenyl sulfone and which provides for the efficient conversion of the hydroxy-substituted aromatic compound to the corresponding metal salt. In some embodiments the temperature is from 140° C. to 250° C., from 140 to 200° C., or from 140 to 190° C., preferably from 160 to 180° C.

The contacting of the hydroxy-substituted aromatic compound with the base is performed in the molten diphenyl sulfone, sulfolane, or a combination comprising at least one of the foregoing for a period of time sufficient to obtain the desired degree of conversion to the metal salt. The contact time depends upon a number of factors including, but not limited to, the amounts of hydroxy-substituted aromatic compound and the base employed. In a particular embodiment the contact time is for greater than 1 hour, for example for 1.5 hours to 5 hours. Appropriate contact times depend upon reaction temperatures and the nature of the reactants, and this can be determined by one skilled in the art, without undue experimentation.

The contacting of the hydroxy-substituted aromatic compound with the base in molten diphenyl sulfone, sulfolane, or a combination comprising at least one of the foregoing can be performed under an inert atmosphere, such as under nitrogen, argon, or helium.

The inventors hereof have developed methods to analyze the residual molar percent of hydroxy-substituted aromatic compound in the reaction mixture. Where the hydroxy-substituted aromatic compound is a dihydroxy-substituted aromatic compound, the method can also determine the molar percent of the mono-protonated salt, i.e., a salt wherein only one of the two protons in the hydroxy groups is substituted with the metal ion.

The method comprises contacting a sample to be analyzed, for example, a sample taken from the reaction mixture, with a methylation agent reactive with the metal salt of an aromatic hydroxyl group but not the hydroxyl group, and analyzing the reaction products to determine the molar percent of hydroxy-substituted aromatic compound in the sample. In some embodiments, the method comprises contacting a sample to be analyzed with the methylation agent; contacting the methylation product with a solvent to provide a diluted product; filtering the diluted product to provide a filtrate; and analyzing the filtrate by liquid chromatography. Once the stoichiometric ratio of the hydroxy-substituted compound to the metal salts thereof during the reaction is determined, if necessary, the stoichiometric ratio can be adjusted by adding additional hydroxy-substituted aromatic compound or base.

The sample to be analyzed comprises at least one of hydroxy-substituted aromatic compounds and salts of the hydroxy-substituted aromatic compounds, including mono-protonated salts.

A suitable methylation agent is methyl methanesulfonate. An excess amount of methyl methanesulfonate can be used in order to ensure that the salts of the hydroxy-substituted aromatic compounds are completely methylated. Methyl methanesulfonate can also be used as a solvent for the methylation reaction.

To facilitate the conversion of the salts of the hydroxy-substituted aromatic compounds to the corresponding methylated products, the sample is contacted with methyl methanesulfonate at an elevated temperature, for example, 30° C. to 165° C.

Once the methylation products are formed, a solvent can be added to dilute the methylation product. The solvent is not particularly limited and includes those that do not interfere with the subsequent liquid chromatography analysis. Exemplary solvent includes acetonitrile, methanol, and the like. The diluted product can be filtered, and the filtrate is then analyzed by liquid chromatography, such as high performance liquid chromatography or ultra-performance liquid chromatography. The amount of the hydroxy-substituted aromatic compound relative to the salts of the hydroxy-substituted aromatic compound in the sample can be determined by known methods, for example by comparison to an internal standard and/or calibration curves for the hydroxy-substituted aromatic compound and the corresponding mono-methylated and di-methylated compounds.

As a specific example, when treated with methyl methanesulfonate, bisphenol A salts are converted to the corresponding methylated products while bisphenol A remains the same. The methylation products are illustrated in Scheme 1. In Scheme 1, "M" represents a metal.

Scheme 1

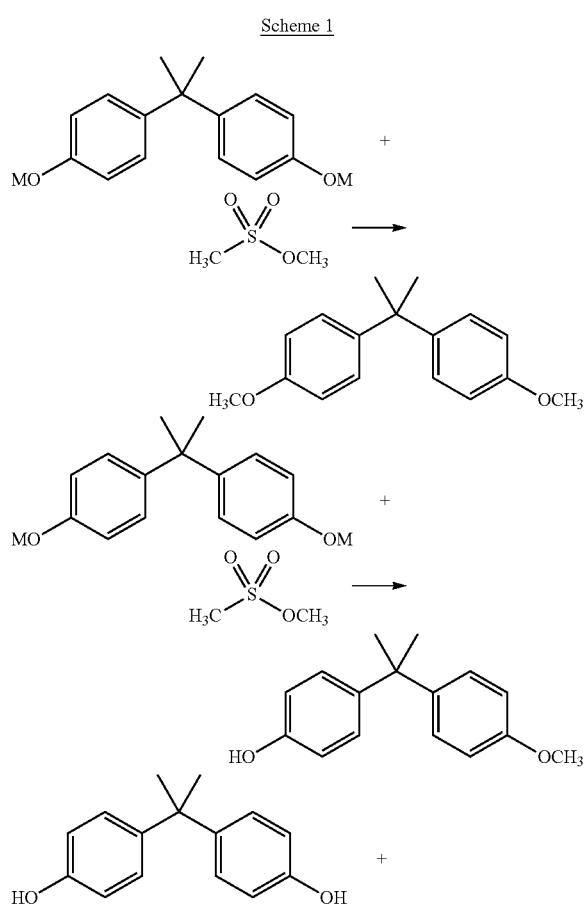

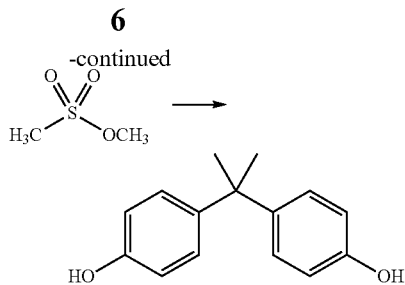

The methylation products can be analyzed by high performance liquid chromatography to quantify bisphenol A, monomethyl bisphenol A, and dimethyl bisphenol A using diphenyl sulfone as the internal standard. The amount of bisphenol A, monomethyl phenol A, and dimethyl bisphenol A per grams of diphenyl sulfone can be converted to molar percent of bisphenol A and molar percent of its salts, and the amount of base adjusted to achieve the desired stoichiometry.

During or after the reaction is complete, water generated from the reaction can be removed from the reaction by simple distillation, for example via a vapor handling system. In some embodiments, the reactor is equipped with a vapor handling system comprising a partial reflux condenser. The vapor stream that is formed during the reaction is introduced into the vapor handling system. The partial reflux condenser is maintained at a temperature below the boiling point of diphenyl sulfone, hydroxy-substituted aromatic compound, and the base under the prevailing conditions (e.g., temperature and pressure) and above the boiling point of water under the prevailing conditions, which results in the removal of water from the reaction mixture. In some embodiments, the temperature of the partial reflux condenser is from 100° C. to 150° C. under atmospheric pressure, which is high enough for water vapor to pass through and low enough for the reactants and diphenyl sulfone to condense within the partial reflux condenser.

In some embodiments the amount of water remaining in the salt-containing diphenyl sulfone, sulfolane, or a combination comprising at least one of the foregoing is less than 3,000 parts per million by weight (ppm), or less than 1,500, less than 1,000 ppm, or less than 500 ppm. Preferably the amount of water is less than 300 ppm, less than 100 ppm, preferably less than 60 ppm, and more preferably less than 40 ppm with respect to the weight of the dry salt present. The amount of water in the salt-containing diphenyl sulfone, sulfolane, or a combination comprising at least one of the foregoing can be determined using known methods.

Remaining traces of water-immiscible solvent in the salt can be removed, if desired, by methods such as vacuum drying, drying under nitrogen or similar operation. It is, however, often convenient to employ the salt in diphenyl sulfone, sulfolane, or a combination comprising at least one of the foregoing without isolation of the salt. For example, the salt can be employed in diphenyl sulfone, sulfolane, or a combination comprising at least one of the foregoing in a subsequent reaction in which the salt is a reactant.

The process for making metal salt described herein can be performed in batch mode, continuous mode or semi-continuous mode. The metal salt of hydroxy-substituted aromatic compound in diphenyl sulfone, sulfolane, or a combination comprising at least one of the foregoing can be used in one or more subsequent reactions to form materials incorporating structural units derived from the hydroxy-substituted aromatic compound. In a specific embodiment, the metal salt in diphenyl sulfone, sulfolane, or a combination comprising at least one of the foregoing can be used directly as a monomer in condensation polymerization.

The metal salt of hydroxy-substituted aromatic compound in diphenyl sulfone, sulfolane, or a combination comprising at least one of the foregoing can be used directly as a monomer in the preparation of polyethers such as, but not limited to, polyetherimides, polyethersulfones, polyetherimidesulfones, polyetherketones, polyetheretherketones, and the like. In an illustrative example the bis(sodium) salt or bis(potassium) salt of a dihydroxy-substituted aromatic compound such as bisphenol A can be used as a monomer to form a polyetherimide through reaction with at least one substituted bis(phthalimide) such as a bis(N-(substituted phthalimido))aromatic compound. Suitable substituents on the bis(N-(substituted phthalimido))aromatic compounds include any that can be displaced in a polymerization reaction with the metal salt of a hydroxy-substituted aromatic compound. In particular embodiments suitable substituents include, but are not limited to, nitro, halogen, chloro, and bromo. Advantageously, the polymerization reaction can be carried out without using any phase transfer catalyst.

The polymerization reaction can be performed in at least one solvent of low polarity. In various embodiments the solvent has a boiling point above 150° C. in order to facilitate the displacement reaction which typically requires temperatures of 125° C. to 250° C. Suitable solvents of this type include, but are not limited to, ortho-dichlorobenzene, para-dichlorobenzene, dichlorotoluene, 1,2,4-trichlorobenzene, diphenyl sulfone, phenetole, anisole, veratrole, or a combination comprising at least one of the foregoing.

Advantageously, no additional solvent is needed since the metal salt of hydroxy-substituted aromatic compound is produced in diphenyl sulfone, which can be used as the solvent for replacement polymerization reaction. In a further advantageous feature, Applicants found that the displacement polymerization reaction can be conducted without using any phase transfer catalyst. If desirable, a phase transfer catalyst can be present.

It is appreciated that in some embodiments, tetramethylene sulfone (sulfolane) can be used as an alternative to diphenyl sulfone. Accordingly, whenever diphenyl sulfone is mentioned, it can be replaced with tetramethylene sulfone (sulfolane).

The methods of the manufacture of salts of hydroxy-substituted compounds and the methods of the manufacture of polyetherimide from the produced salts are further illustrated by the following non-limiting examples.

EXAMPLES

Materials

The materials in Table 1 were used or made in the following Examples.

TABLE 1

| Acronym | Description | Source |
|---------|-------------|--------|
| BPA | 2,2-Bis(4-hydroxyphenyl)propane, (Bisphenol A) | Hexion |
| $K_2$BPA | Bisphenol, dipotassium salt | Examples |
| KOH | Potassium hydroxide | Acculute |
| DPS | Diphenyl sulfone | |
| MMS | Methyl methanesulfonate | Aldrich |
| ClPA | Mixture of 3-chlorophthalic anhydride and 4-chlorophthalic anhydride | SABIC |
| mPD | meta-Phenylene diamine | DuPont |

TABLE 1-continued

| Acronym | Description | Source |
|---------|-------------|--------|
| AcOH | Acetic acid | Aldrich |
| ClPAMI | 1,3-Bis[N-(4-chlorophthalimido)]benzene | Examples |
| PEI | Polyetherimide | Examples |
| $H_3PO_4$ | Phosphoric acid | Fischer |

Property Testing

Gel Permeation Chromatography (GPC) analysis was conducted as follows. In a 20 ml glass vial, about 20 mg of the polymer sample was taken and dissolved into a quench solution (3.5 L $CH_2Cl_2$+120 mL AcOH+30 mL o-DCB) followed by filtration with 0.25 micron filter into an HPLC vial. The solution was analyzed by GPC with polystyrene standard (HPLC 2695, Waters GPC software using 2487 Dual absorbance detector of wavelength 254 nm and Mixed Bed C, PLgel 5 micrometers, 300×7.5 mm, P/N 1110-6500 column).

The amount of base can be determined by titration (e.g., against aqueous HCl) to determine excess equivalents of base (sodium phenate and excess alkali metal hydroxide).

Example 1

Synthesis of $K_2$BPA in Diphenyl Sulfone

A 500 mL 3-neck round bottomed flask (24/40) was equipped with an overhead stirrer through its center joint. One of the side joints was connected to a nitrogen sweep while the other was connected to a nitrogen blanket connected to a bubbler via a Dean-Stark trap with its arm wrapped in a heating tape. The flask was then immersed into an oil bath at 170° C. and DPS (80 g) was added. Once the DPS was completely molten, the stirrer was turned on and solid KOH pellets (6.003 g, 0.092 moles, 86% solid, 2.0 equiv.) were added and stirring continued for 10 min. KOH dissolved completely into molten DPS. Solid BPA (10.5031 g, 0.046 moles, 1.0 equiv.) was added into the solution and stirring was continued for 3 h. A thick slurry was formed with water stripping off in the form of droplets into the Dean-Stark trap. The slurry was subjected to BPA stoichiometry analysis.

Example 2

Stoichiometry Analysis of the Salt Made in Example 1

The salt slurry sample from example 1 (50 mg) was taken into a 20-mL glass vial, and 100 mg methyl mesylate was added. The vial was flushed with nitrogen briefly and capped. The vial was then placed a heat block at 170° C. The methylation was completed in 5-10 min. After cooling the vial, 5 mL acetonitrile was added; and the mixture was sonicated for 5 min. The suspension was filtered into a HPLC vial and run in high performance liquid chromatograph (UPLC) calibrated for quantification of BPA ("$BPA_{quant}$") as determined by the stoichiometry method described herein, monomethyl BPA (MMBPA) and dimethyl BPA (DMBPA) using DPS as internal standard. The UPLC reading provided mg/grams of DPS of the methylated products of the mixture which was then converted into the moles and then the molar ratios of BPA:MMBPA:DMBPA. The excess of total BPA mol % present and the amount of KOH needed for the correction was then calculated. The calculations are shown below and exemplary results are shown in Table 2, where the BPA stoichiometry is 0.581.

Mol % BPA (excess)=(moles of BPA$_{quant}$/total moles of BPA charged to reaction)×100.

Mol % MMBPA (excess)=(moles of MMBPA $_{ant}$/total moles of BPA charged to reaction)×100.

BPA stoichiometry=Mol % of BPA (excess)+(mol % of MMBPA (excess)/2)

20.1173 g of the dry powdered ClPAMI (0.046 moles, 1.0 equiv.) was weighed and added to the salt (0.046 moles, 1.0 equiv., 0.58 mol % BPA excess) prepared in example 1. The temperature of the reaction mixture was increased from 170° C. to 200° C. The mixture first became thick solid and slowly converted into the slurry and then became thinner. Mw build was monitored by GPC analysis of a 50-mg sample taken in a 20 ml glass vial and dissolved into 5 mL of a quench solution (3.5 L $CH_2Cl_2$+120 mL AcOH+30 mL

TABLE 2

Calculator to convert the methylated products into the BPA stoichiometry

| Components | Mw | moles | grams | % solid | Components | Mw | mmoles | mole % | HPLC mg/g (DPS) | DPS (grams) | <OH addition (mg) | BPA addition (mg) |
|---|---|---|---|---|---|---|---|---|---|---|---|---|
| DPS | | | 80 | 25.39858 | BPA | 228.3 | 0.1363 | 0.2963 | 0.389 | 80 | | 132.6020 |
| Potassium hydroxide | 56.1056 | 0.092015 | 6.003 | 86 | MMBPA | 242.3 | 0.2618 | 0.5691 | 0.793 | 80 | | if − ve |
| Potassium carbonate | 138.205 | 0 | 0 | | DMBPA | 256.3 | 43.1449 | 99.1346 | 138.22 | 80 | | |
| Sodium hydroxide | 39.997 | 0 | 0 | | KOH short | 34.4 | 0.5345 | 1.1617 | | 80 | 39.9624 | |
| BPA | 228.29 | 0.046008 | 10.5031 | | Excess OH moles | | 0.5345 | | BPA Stoich | 0.5801 | if + ye | |

To determine the time required for the salt formation reaction to complete, samples were taken from the reaction mixture of example 1 at different time intervals and analyzed for residual BPA molar percent. The results are shown in FIG. 1. As shown in FIG. 1, the salt formation reaction is complete in about 3 hours.

Example 3

Synthesis of Polyetherimide

The example demonstrates the polymerization of the $K_2BPA$ salt made in Example 1 with ClPAMI in DPS to make polyetherimide without using any phase transfer catalyst (PTC). The example also shows the control of Mw of the polyetherimide polymer by varying the stoichiometry of the $K_2BPA$ salt (i.e., varying the ratio of ratio of BPA and KOH).

Figure 2:
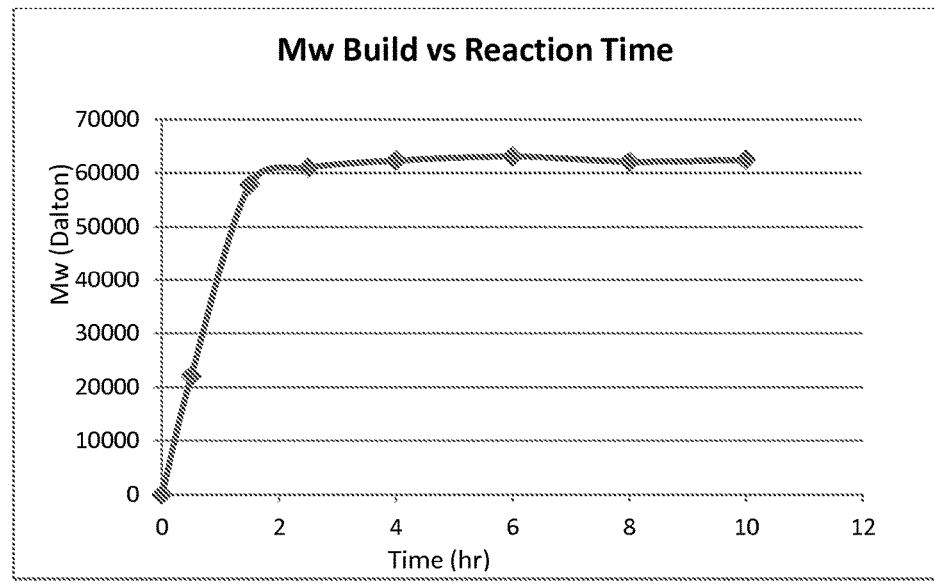
FIG. 2 is a graph of Mw of polyetherimide as a function of time.

A 3-neck 1 L round-bottomed flask was equipped with an overhead stirrer and two nitrogen outlets which were connected to a nitrogen sweep and a nitrogen blanket via a Dean-Stark trap and condenser. Chlorophthalic anhydride (ClPA) (35.028 g, 0.1919 moles, 2.008 equiv) and metaphenylene diamine (mPD) (10.333 g, 0.0955 moles, 1.0 equiv, APHA=35) were charged under nitrogen. o-DCB (288 mL) was degassed at 130° C. in a separate 3-neck flask for at least 30 min. The degassed o-DCB was cannulated into the flask (to make a 10% solid mixture). The reaction flask was then immersed into the oil bath and heated to 145° C. The reaction generated a gel when the temperature reached 125° C. Slow and continuous heating/stirring (100-150 rpm) broke the gel into a slurry. The temperature of the oil bath was increased to 185° C.; and the reaction mixture was stirred for a total of 6 h. Stripping off 77 mL o-DCB (and water) provided a ClPAMI slurry in o-DCB with a 13% solids content. The ClPAMI slurry in o-DCB was filtered through a 2.7 micron filter paper in a Buchner Funnel and the solid residue was washed with 100 mL warm o-DCB (100° C.). The filtered solid was then dried in a vacuum oven at 160° C. for 14 h. The dry solid was crushed into powder. Karl-Fisher analysis was used to test the moisture content (<80 ppm).

o-DCB) followed by filtration. The solution was analyzed by GPC column with polystyrene standard. The results are shown in FIG. 2.

The reaction was quenched with phosphoric acid (85%, 670 mg) at 170° C. and stirred for 30 min. The mixture was then transferred into a 500 mL flask with a Teflon cap and cooled. Methylene chloride (200 mL) was added into the solidified polymer solution. The mixture was shaken to convert the solid into a suspension. The suspension was filtered through 2.7 micron filter paper in a Buchner Funnel to remove the precipitated solid. The clear polymer solution in DPS and methylene chloride was slowly added to 500 mL acetone with constant agitation by a homogenizer to precipitate the polyetherimide which was filtered and washed twice with 500 mL acetone each to provide a polyetherimide powder, which was subsequently dried in vacuum at room temperature.

Table 3 summarizes the results of the polymerizations that were performed using the same procedure except that the salt stoichiometry was varied in order to investigate the effect of salt stoichiometry on the ultimate Mw of the polyetherimide. In all reactions the molar ratio of salt/ClPAMI was 1:1.

TABLE 3

| BPA Stoichiometry | Mw | PDI | Mz/Mw |
|---|---|---|---|
| 0.09 | 26416 | 2.27 | 1.55 |
| 0.19 | 43219 | 2.53 | 1.55 |
| 0.21 | 32529 | 2.17 | 1.54 |
| 0.45 | 49704 | 2.47 | 1.63 |
| 0.53 | 58938 | 2.53 | 1.62 |
| 0.575 | 51837 | 2.62 | 1.56 |
| 0.595 | 62478 | 2.71 | 1.51 |
| 0.76 | 55256 | 2.69 | 2.03 |
| 0.78 | 91628 | 3.38 | 1.68 |
| 0.835 | 59315 | 2.79 | 1.77 |
| 0.91 | 52031 | 2.46 | 1.48 |
| 0.965 | 63992 | 2.52 | 1.52 |
| 0.98 | 51237 | 2.48 | 1.63 |
| 1.11 | 43013 | 2.48 | 1.53 |

TABLE 3-continued

| BPA Stoichiometry | Mw | PDI | Mz/Mw |
|---|---|---|---|
| 1.175 | 55392 | 2.43 | 1.64 |
| 1.665 | 33105 | 2.24 | 1.51 |
| 2.275 | 43620 | 2.56 | 1.55 |
| 3.07 | 24915 | 2.48 | 1.52 |
| 6.29 | 13571 | 2.04 | 1.59 |

Figure 3:
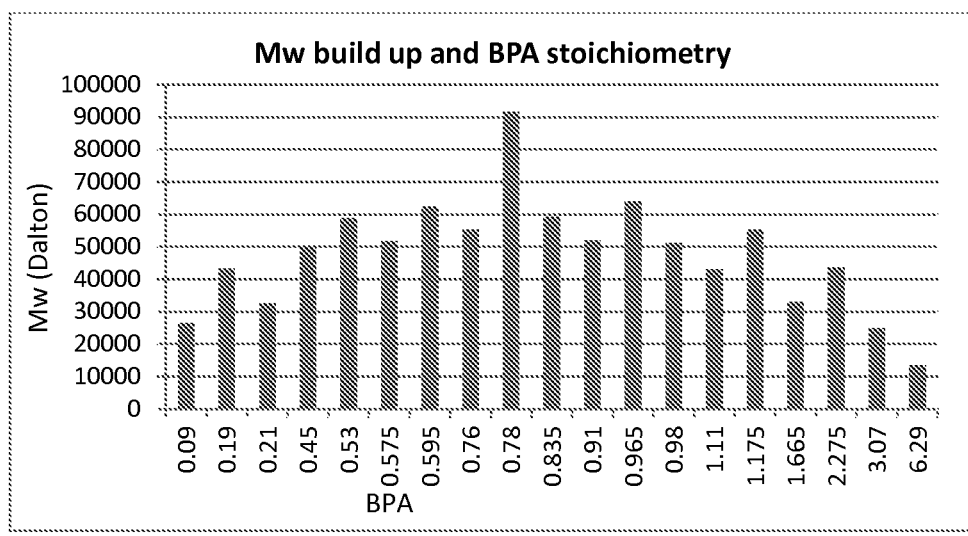
FIG. 3 is a graph of Mw of polyetherimide as a function of BPA stoichiometry.

The Mw distribution against BPA stoichiometry from Table 3 is plotted in FIG. 3. When the stoichiometry is 0.78, the Mw of polyetherimide is about 90000. The Mw decrease with the increase of BPA stoichiometry. The Mw also decrease with the decrease of BPA stoichiometry. Without wishing to be bound by theory, it is believed that the trend observed at lower BPA stoichiometry may be due to the presence of unreacted KOH which could react with ClPAMI, thereby rendering it off-stoichiometry, which results in lower molecular weight.

Embodiment 1: A method for the manufacture of a metal salt of a hydroxy-substituted aromatic compound, the method comprising: contacting a hydroxy-substituted aromatic compound with a base comprising a metal cation in molten diphenyl sulfone or sulfolane to provide a mixture comprising water, diphenyl sulfone, or sulfolane, and a metal salt of the hydroxy-substituted aromatic compound; and removing water from the mixture in the absence of an azeotrope solvent to form the metal salt of the hydroxy-substituted aromatic compound, wherein the metal salt of the hydroxy-substituted aromatic compound comprises less than 3,000 ppm of water.

Embodiment 2: The method of Embodiment 1, wherein the hydroxyl-substituted aromatic compound is at least one dihydroxy-substituted aromatic compound having formula

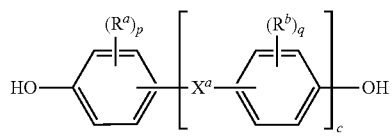

wherein $R^a$ and $R^b$ are each independently a halogen atom or a monovalent hydrocarbon group; p and q are each independently integers of 0 to 4; c is 0 to 4; and $X^a$ is a single bond, —O—, —S—, —S(O)—, —S(O)$_2$—, —C(O)—, or a $C_{1-18}$ organic bridging group.

Embodiment 3: The method of Embodiment 1 or Embodiment 2, wherein the hydroxyl-substituted aromatic compound is 2,2-bis(4-hydroxyphenyl)propane or 4,4'-dihydroxybiphenyl.

Embodiment 4: The method of any one or more of Embodiments 1 to 3, wherein the base is an alkali hydroxide, an alkali carbonate, an alkali bicarbonate, or a combination comprising at least one of the foregoing.

Embodiment 5: The method of any one or more of Embodiments 1 to 4, wherein the base is sodium hydroxide or potassium hydroxide.

Embodiment 6: The method of any one or more of Embodiments 1 to 5, wherein the base and the hydroxy-substituted aromatic compound are present in amounts corresponding to a molar ratio of the base to the hydroxy-substituted aromatic compound which deviates from ideal stoichiometry by no more than 5 mole %.

Embodiment 7: The method of Embodiment 1, wherein $$\frac{\text{weight of hydroxy-substituted aromatic compound}}{\text{weight of hydroxy-substituted aromatic compound}+\text{weight of diphenyl sulphone or sulfolane}}(100)$$

is 1 to 30%, specifically 15 to 25%, preferably 18 to 22%.

Embodiment 8: The method of any one or more of Embodiments 1 to 7, wherein the contacting is carried out at a temperature in a range from 140° C. to 250° C.

Embodiment 9: The method of any one or more of Embodiments 1 to 8, wherein the contacting is carried out under an inert atmosphere.

Embodiment 10: The method of any one or more of Embodiments 1 to 9, wherein the contacting comprises adding the base in a solid form to molten diphenyl sulfone to provide a solution; and adding the hydroxy-substituted compound to the solution.

Embodiment 11: The method of any one or more of Embodiments 1 to 10, wherein water is removed from the mixture by distillation.

Embodiment 12: The method of any one or more of Embodiments 1 to 11, further comprising determining the stoichiometry of the hydroxy-substituted compound relative to the metal salts thereof; and optionally adjusting the stoichiometry of the hydroxy-substituted compound relative to the base.

Embodiment 13: The method of Embodiment 12, wherein determining the stoichiometry of the hydroxy-substituted compound relative to the base comprises contacting the mixture comprising water, diphenyl sulfone, and a metal salt of the hydroxy-substituted aromatic compound with a methylating agent selective for methylation of aromatic hydroxyl salts to provide a methylation product mixture; and determining the molar ratio of the hydroxy-substituted aromatic compound to one or of methylated hydroxy-substituted aromatic compounds in the methylation product mixture.

Embodiment 14: The method of Embodiment 13, wherein the methylation agent is methyl methane sulfonate.

Embodiment 15: The method of any one or more of Embodiments 13 to 14, wherein the determining the molar ratio comprises contacting the methylation product mixture with a solvent to provide a diluted product; filtering the diluted product to provide a filtrate; determining a relative amount of the hydroxy-substituted aromatic compound to the one or more methylated hydroxy-substituted aromatic compounds in the filtrate by liquid chromatography; and calculating the molar ratio of the hydroxy-substituted aromatic compound to the one or more methylated hydroxy-substituted aromatic compounds based on the relative amounts.

Embodiment 16: A method for the manufacture of a polyetherimide composition, the method comprising: polymerizing a substituted bis(phthalimide) and the metal salt of the dihydroxy aromatic compound of any one or more of Embodiments 1 to 15 in the presence of diphenyl sulfone, sulfolane, or a combination comprising at least one of the foregoing solvent to form a polyetherimide composition.

Embodiment 17: The method of Embodiment 16, wherein the metal salt of the dihydroxy aromatic compound is not isolated from the diphenyl sulfone prior to polymerization.

Embodiment 18: The method of Embodiment 16 or Embodiment 17, wherein the polymerization is carried out without a phase transfer catalyst.

Embodiment 19: The method of Embodiment 16 or 17, wherein the polymerization is carried out in the presence of a phase transfer catalyst.

The singular forms "a," "an," and "the" include plural referents unless the context clearly dictates otherwise. "Or" means "and/or." The endpoints of all ranges directed to the same component or property are inclusive and independently combinable. Unless defined otherwise, technical and scientific terms used herein have the same meaning as is commonly understood by one of skill in the art to which this invention belongs. As used herein, a "combination" is inclusive of blends, mixtures, alloys, reaction products, and the like.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "aryl" refers to an aromatic monovalent group containing only carbon in the aromatic ring or rings; "arylene" refers to an aromatic divalent group containing only carbon in the aromatic ring or rings; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylenearyl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a polyetherimide composition, the method comprising:
   contacting a hydroxy-substituted aromatic compound with a base comprising a metal cation in molten diphenyl sulfone or sulfolane to provide a mixture comprising water, diphenyl sulfone, or sulfolane, and a metal salt of the hydroxy-substituted aromatic compound;
   removing water from the mixture in the absence of an azeotrope solvent to form the metal salt of the hydroxy-substituted aromatic compound, wherein the metal salt of the hydroxy-substituted aromatic compound comprises less than 3,000 ppm of water; determining the stoichiometry of the hydroxy-substituted compound relative to the metal salts thereof, wherein determining the stoichiometry of the hydroxy-substituted compound relative to the base comprises contacting the mixture comprising water, diphenyl sulfone, and a metal salt of the hydroxy-substituted aromatic compound with a methylating agent selective for methylation of aromatic hydroxyl salts to provide a methylation product mixture; and determining the molar ratio of the hydroxy-substituted aromatic compound to one or of methylated hydroxy-substituted aromatic compounds in the methylation product mixture; optionally adjusting the stoichiometry of the hydroxy-substituted compound relative to the base; and
   polymerizing a substituted bis(phthalimide) and the metal salt of the dihydroxy aromatic compound in the presence of diphenyl sulfone, sulfolane, or a combination comprising at least one of the foregoing solvent to form a polyetherimide composition.

2. The method of claim 1, wherein the hydroxyl-substituted aromatic compound is at least one dihydroxy-substituted aromatic compound having formula

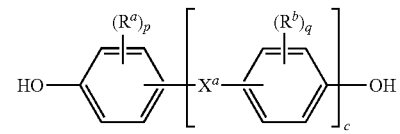

wherein $R^a$ and $R^b$ are each independently a halogen atom or a monovalent hydrocarbon group; p and q are each independently integers of 0 to 4; c is 0 to 4; and $X^a$ is a single bond, —O—, —S—, —S(O)—, —S(O)$_2$—, —C(O)—, or a $C_{1-18}$ organic bridging group.

3. The method of claim 1, wherein the hydroxyl-substituted aromatic compound is 2,2-bis(4-hydroxyphenyl)propane or 4,4'-dihydroxybiphenyl.

4. The method of claim 1, wherein the base is an alkali hydroxide, an alkali carbonate, an alkali bicarbonate, or a combination comprising at least one of the foregoing.

5. The method of claim 1, wherein the base is sodium hydroxide or potassium hydroxide.

6. The method of claim 1, wherein the base and the hydroxy-substituted aromatic compound are present in amounts corresponding to a molar ratio of the base to the hydroxy-substituted aromatic compound which deviates from ideal stoichiometry by no more than 5 mole %.

7. The method of claim 1, wherein $$\frac{\text{weight of hydroxy-substituted aromatic compound}}{\text{weight of hydroxy-substituted aromatic compound} + \text{weight of diphenyl sulphone or sulfolane}}(100)$$

is 1 to 30%.

8. The method of claim 1, wherein the contacting is carried out at a temperature in a range from 140° C. to 250° C.

9. The method of claim 1, wherein the contacting is carried out under an inert atmosphere.

10. The method of claim 1, wherein the contacting comprises adding the base in a solid form to molten diphenyl sulfone to provide a solution; and adding the hydroxy-substituted compound to the solution.

11. The method of claim 1, wherein water is removed from the mixture by distillation.

12. The method of claim 1, wherein the metal salt of the dihydroxy aromatic compound is not isolated from the diphenyl sulfone prior to polymerization.

13. The method of claim 1, wherein the polymerization is carried out without a phase transfer catalyst.

14. The method of claim 1, wherein the polymerization is carried out in the presence of a phase transfer catalyst.

15. The method of claim 1, wherein the methylation agent is methyl methane sulfonate.

* * * * *